United States Patent [19]

Ahari

[11] Patent Number: 4,749,572
[45] Date of Patent: Jun. 7, 1988

[54] PHARMACEUTICAL PREPARATIONS

[75] Inventor: Mahmoud Ahari, Tehran, Iran

[73] Assignee: Pharmaceutical Holdings Limited, Jersey, United Kingdom

[21] Appl. No.: 768,828

[22] Filed: Aug. 21, 1985

[30] Foreign Application Priority Data

Aug. 28, 1984 [GB] United Kingdom ............. 8421706

[51] Int. Cl.$^4$ .................. A61K 33/38; A61K 35/78
[52] U.S. Cl. .............................. 424/132; 424/195.1; 424/DIG. 13; 424/450; 424/464; 514/861; 514/925; 514/926; 514/927; 514/928
[58] Field of Search ........... 424/132, 195.1, DIG. 13, 424/450, 464; 514/861, 925, 926, 927, 928

[56] References Cited

FOREIGN PATENT DOCUMENTS 1661192 8/1969 United Kingdom .

OTHER PUBLICATIONS

Handbook of Nonprescription Drugs 6th ed. 19, pp. 341 and 342.
Merck Index, 9th ed. 1976, p. 1101, No. 8261.
Lewis, Medical Botany, Wiley & Sons, NY, NY., p. 342, 1977.
Remington's Pharm. Science 15th ed. 1975, p. 89.

Primary Examiner—J. R. Brown
Assistant Examiner—John W. Rollins, Jr.
Attorney, Agent, or Firm—Spencer & Frank

[57] ABSTRACT

A pharmaceutical preparation for the treatment of, e.g. ulcers, burns and skin diseases contains, as essential ingredients, from 5 to 25% by weight of Peru Balsam and from 0.01 to 0.20% by weight of silver nitrate. The preparation may be administered enterally or topically.

20 Claims, No Drawings

PHARMACEUTICAL PREPARATIONS

FIELD OF THE INVENTION

This invention relates to pharmaceutical preparations. The invention is especially concerned with pharmaceutical preparations which are suitable for topical and body cavity administration in humans and animals, for the treatment and healing of abscesses, lacerations, ulcers, e.g. duodenal and gastric ulcers, and also in the treatment of burns and skin diseases such as herpes, eczema and nappy rash.

TECHNOLOGY REVIEW

Peru (or Peruvian) Balsam is an oleo-resin obtained from the beaten and scorched bark of the trunk of *Myorxylon Pereirae*, a tree grown in San Julian, El Salvador and Nicaragua.

It is known that this material is useful in compositions for the debriding and healing of wounds (see, for example, No. GB-A-1,161,192).

The pharmaceutical preparations of the invention can be used for both topical and systematic therapy. For topical application they can take the form of ointments, creams, solutions or suspensions, for example; for systematic administration they may be in the form, for example, of tablets, capsules, dragees, syrups, solutions and suspensions. They will contain one or more pharmaceutically-acceptable adjuvants, of which many suitable types are known in the art. Tablets, for example, may contain one or more fillers and/or binding agents.

SUMMARY OF THE INVENTION

The invention provides a pharmaceutical preparation comprising from 5 to 25 percent by weight of Peru Balsam and from 0.01 to 0.20 percent by weight of silver nitrate, together with a pharmaceutically acceptable carrier or diluent.

DETAILED DESCRIPTION OF THE INVENTION

It is believed that stomach ulcers are caused by a virus which enters the inner skin of the stomach and the duodenum and then starts to reproduce and secrete a poison which alters the structure of the stomach. In order to repel this, the inner skin starts to form a band of flesh around the affected areas. When excessive reproduction of the virus starts to over-spill the excess flesh, bleeding occcurs. This ceases immediately the virus is removed, e.g. by washing, and the pain felt by the patient during bleeding does not recur until the next incidence of virus reproduction.

A preparation according to the invention which is especially effective in the treatment of stomach ulcers comprises from 5 to 25% by weight of Peru Balsam, from 0.01 to 0.20% by weight of silver nitrate, from 1 to 10% by weight oxidised salt and from 1 to 10% by weight oxidised flour.

Such a preparation is suitably put up in the form of tablets, and thus may contain the usual additives and excipients used in tablet formation. The tablets thus also preferably include starch, which is used as a binding agent to form the tablets into the required shape, the starch being present in an amount up to 80% by weight dependent on the required size of the tablets.

Of the essential ingredients of the ulcer-treating preparation, it is believed that the silver nitrate has the effect of destroying the virus; the other ingredients both destroy the virus and assist the healing of the inner skin of the stomach.

Thus, the preparation begins to destroy the virus as soon as it enters the stomach, gradually halts the bleeding and assists the healing process of the inner skin. A particular advantage of the ulcer-treating preparation is that it does not prevent normal acidic secretions in the stomach.

Pharmaceutical preparations according to the invention are also useful in the treatment of skin burns and other skin diseases and conditions. Thus, in the case of skin burns, the viruses existing in the atmosphere attach themselves to the skin where it is burnt and start rapid reproduction. The body's defences fight back by producing new flesh, which tends to surround the virus by encircling the burn and pulling the existing flesh around it in order to cover and protect the burn. This pulling action affects the surrounding muscles and skin, and is the cause of body and skin disfigurement which is common in major skin burns. The body defence system also produces excessive flesh on and around the burn, which traps the virus and eventually destroys it but leaves the skin disfigured. Skin diseases such as herpes, e.g. genital herpes, are also caused by viruses.

Burns and other skin diseases may be treated by a pharmaceutical preparation comprising from 5 to 25% by weight of Peru Balsam and from 0.01 to 0.20% by weight of silver nitrate, together with a pharmaceutically acceptable carrier or diluent.

The preparation for treating skin ailments is preferably in the form of a viscous liquid such as an oil, ointment or cream, and for this purpose the composition suitably comprises from 20 to 70% by weight petroleum jelly (e.g. Vaseline) and/or from 5 to 30% by weight lanoline and/or from 5 to 30% by weight animal fat (cow) and/or from 5 to 30% by weight animal fat (sheep).

In this preparation the silver nitrate has the effect of destroying the virus, and the Peruvian Balsam destroys the virus, protects the affected area and helps the skin cells to form new skin.

The following Examples are given for the purpose of illustrating the invention.

EXAMPLE 1

A preparation in the tablet form for the treatment of duodenal and gastric ulcers as made from the following ingredients:
Peru Balsam: 20 kg
Silver Nitrate: 0.125 kg
Oxidised Salt: 15 kg
Oxidised Flour: 15 kg
Starch: 150 kg A thick solution of the starch and water was mixed with the Peru Balsam in a 200 kg capacity ordinary pharmaceutical mixer drum, and heated to 50° C. The oxidised salt and oxidised flour (obtained by heating salt and flour separately until they had turned a dark brown colour) were added and well mixed. Silver nitrate crstals were then added, and the mixer continued operating until a homogenous mix was obtained. This was then fed to a tabletting machine, and tablets were produced therefrom.

The dosage rate is suitably of the order of two tablets (each weighing 1 gram per day, and suitably treatment lasts for a period of the order of 30 days. The tablets are beneficial to the digestive system, they prevent heartburn, and they stop excessive stomach gases being produced.

EXAMPLE 2

A composition for the treatment of skin burns and genital herpes was made from the following formulation:-
Peru Balsam: 20 kg
Silver Nitrate: 0.125 kg
Vaseline: 100 kg
Lanoline: 20 kg
Animal Fat-Cow: 30 kg
Animal Fat-Sheep: 30 kg The Vaseline, lanoline and animal fat were mixed with the Peru Balsam in a 200 kg pharmaceutical drum mixer, and the mixture was heated to 50° C. Silver nitrate crystals were then added to the mixture and well mixed in. The resulting homogenous mixture was packaged for use as an ointment.

When this ointment is used for the treatment of skin burns, the area on and around the burn should be cleaned with a weak solution of disinfectant. The ointment is then rubbed on to the affected area each day until the skin is completely healed.

In the treatment of herpes, the affected areas should be cleaned and washed with soap and water every day and the ointment rubbed on until the skin heals completely.

The ointment of the invention prevents disfigurement of muscles and skin, and leaves no marks where the burn or sore appeared. It is more effective than conventional treatments, reducing the treatment time by up to one third when compared with such conventional treatments. It can have the effect of preventing death in many cases where major burns would otherwise cause death.

I claim:

1. A pharmaceutical preparation comprising from 5 to 25% by weight of Peru Balsam and from 0.01 to 0.20% by weight of silver nitrate, together with a pharmaceutically acceptable carrier of diluent.

2. A preparation as claimed in claim 1, containing also from 1 to 10% by weight oxidised salt and from 1 to 10% by weight oxidised flour.

3. A method for the treatment of duodenal and gastric ulcers, comprising administering an effective amount of a pharmaceutical preparation in tablet or capsule form, comprising from 5 to 25% by weight of Peru Balsam and from 0.01 to 0.20% by weight of silver nitrate.

4. A method as claimed in claim 3, containing an effective amount of starch binding said preparation in tablet form.

5. A method as claimed in claim 3, in capsule form.

6. The method of treating duodenal and gastric ulcers set forth in claim 3, wherein said pharmaceutical preparation also contains from 1 to 10% by weight oxidized salt and from 1 to 10% by weight oxidized flour.

7. A method as claimed in claim 6, containing an effective amount of starch binding said preparation in tablet form.

8. A method as claimed in claim 6, in capsule form.

9. A method for the treatment of skin burns, comprising administering an effective amount of a pharmaceutical preparation in an oil, ointment or cream form, comprising from 5 to 25% by weight of Peru Balsam and from 0.12 to 0.20% by weight of silver nitrate.

10. A method as claimed in claim 9 comprising also from 20 to 70% by weight petroleum jelly.

11. A method as claimed in claim 9 containing from 5 to 30% by weight lanoline.

12. A method as claimed in claim 9 containing from 5 to 30% by weight cow fat.

13. A method as claimed in claim 9 containing from 5 to 30% by weight sheep fat.

14. A method as claimed in claim 9 containing from 20 to 70% by weight petroleum jelly and 5 to 30% by weight lanoline.

15. A method as claimed in claim 9 containing from 20 to 70% by weight petroleum jelly and from 5 to 30% by weight cow fat.

16. A method as claimed in claim 9 containing from 20 to 70% by weight petroleum jelly and from 5 to 30% by weight sheep fat.

17. A method as claimed in claim 9 containing from 5 to 30% by weight lanoline and from 5 to 30% by weight cow fat.

18. A method as claimed in claim 9 containing from 5 to 30% by weight lanoline and from 5 to 30% by weight sheep fat.

19. A method as claimed in claim 9 containing from 5 to 30% by weight cow fat and from 5 to 30% by weight sheep fat.

20. A method for the treatment of viral skin diseases, comprising administering an effective amount of a pharmaceutical preparation in an oil, ointment or cream form, comprising from 5 to 25% by weight of Peru Balsam and from 0.12 to 0.20% by weight of silver nitrate.

* * * * *